United States Patent [19]
Jensen

[11] 4,451,258
[45] May 29, 1984

[54] OSTOMY BAG WITH AN ADJUSTABLE VENT

[75] Inventor: Ole R. Jensen, Rivervale, N.J.

[73] Assignee: E. R. Squibb & Sons, Inc., Princeton, N.J.

[21] Appl. No.: 354,772

[22] Filed: Mar. 4, 1982

[51] Int. Cl.³ .............................................. A61F 5/44
[52] U.S. Cl. ................................... 604/333; 55/385 C
[58] Field of Search .............. 604/323, 339, 341, 342, 604/350, 359, 360, 332–338; 55/413, 417, 410, 493, 385 C, 497, DIG. 13, 385 A

[56] References Cited

U.S. PATENT DOCUMENTS

| | | | |
|---|---|---|---|
| 1,646,880 | 10/1927 | Schaffer | 604/359 |
| 3,800,510 | 4/1974 | Lamond | 55/497 |
| 4,232,672 | 11/1980 | Steer et al. | 604/333 |
| 4,268,286 | 5/1981 | Steer et al. | 604/333 |

FOREIGN PATENT DOCUMENTS

| | | | |
|---|---|---|---|
| 2804154 | 1/1979 | Fed. Rep. of Germany | 55/DIG. 13 |
| 2927287 | 2/1981 | Fed. Rep. of Germany | 55/DIG. 13 |
| 576181 | 3/1946 | United Kingdom | 604/332 |

*Primary Examiner*—C. Fred Rosenbaum
*Assistant Examiner*—J. L. Kruter
*Attorney, Agent, or Firm*—Lerner, David, Littenberg, Krumholz & Mentlik

[57] ABSTRACT

An air vent for an ostomy bag has a variable flow rate so that the flow rate through a deodorizing filter housed in the vent can be varied to enhance the effectiveness of the filter. The vent also permits precise control over the degree of inflation of the bag.

15 Claims, 8 Drawing Figures

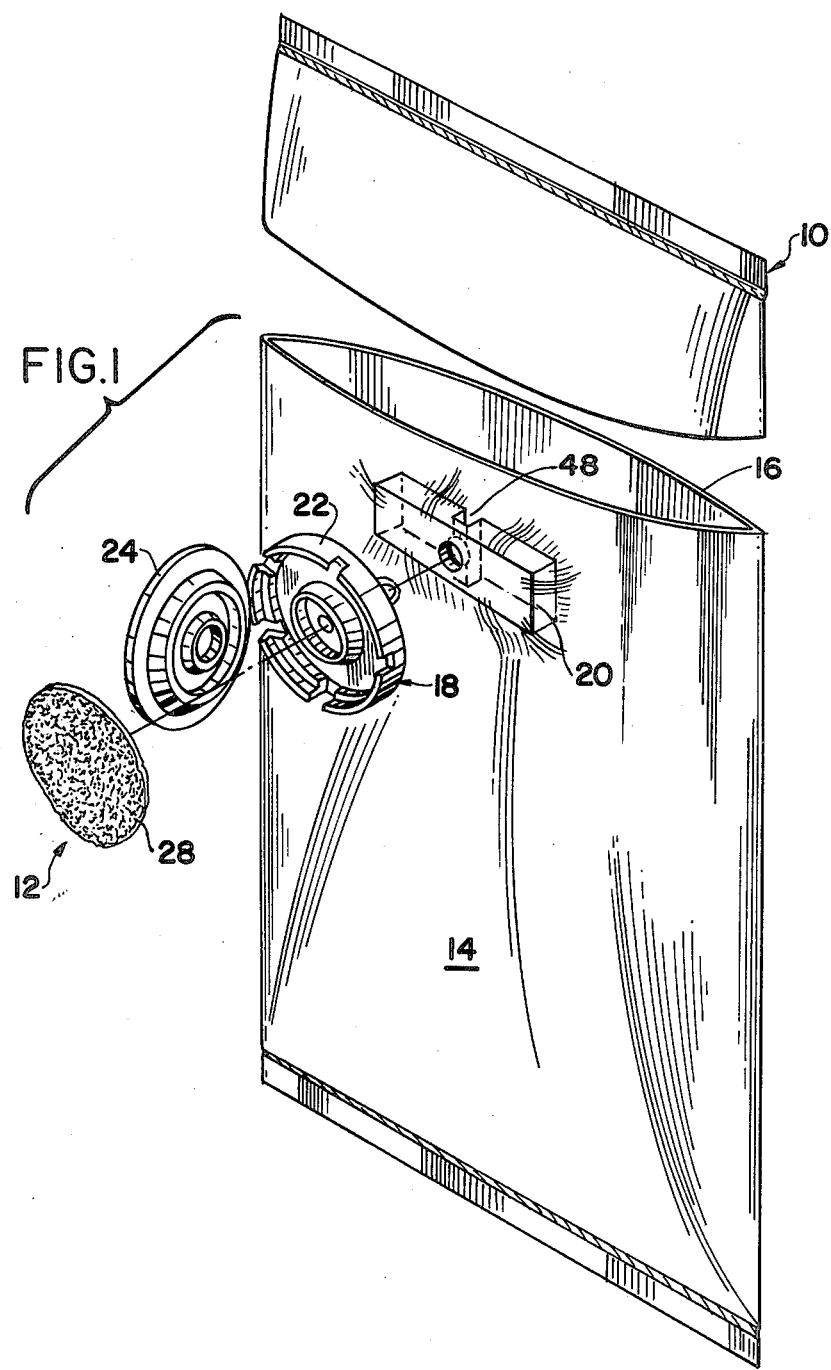

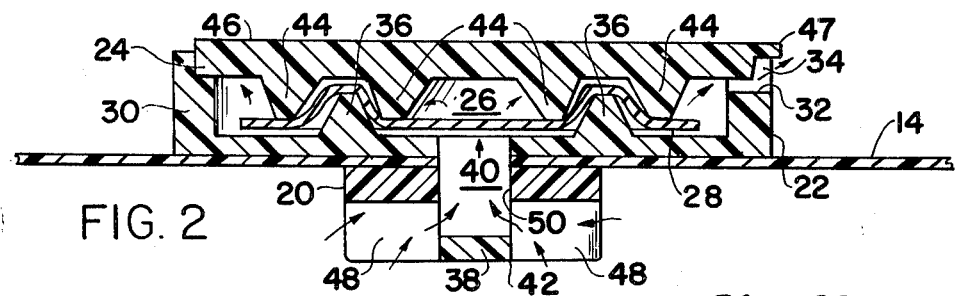
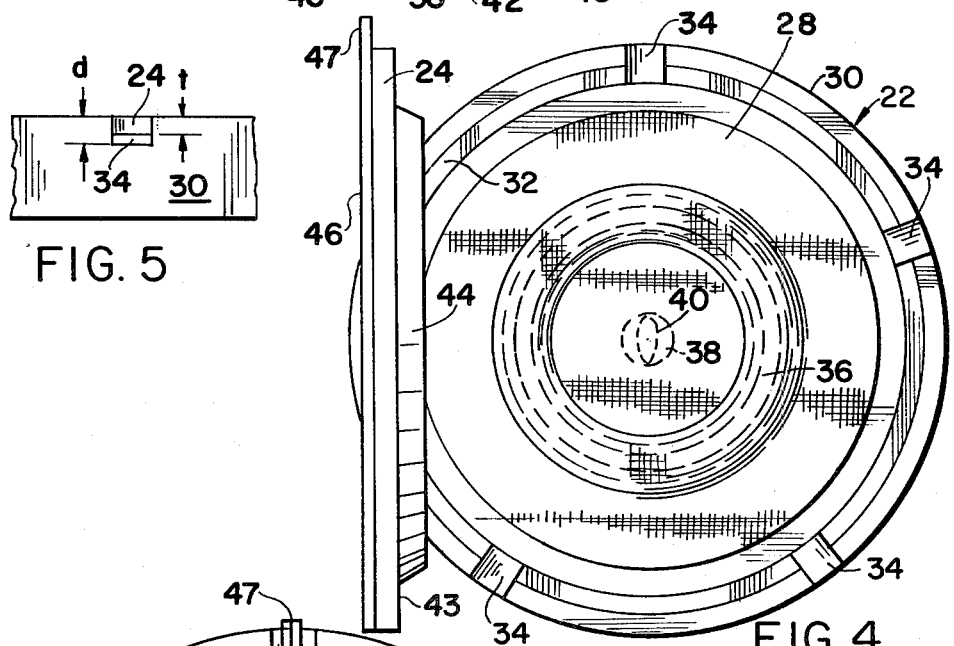
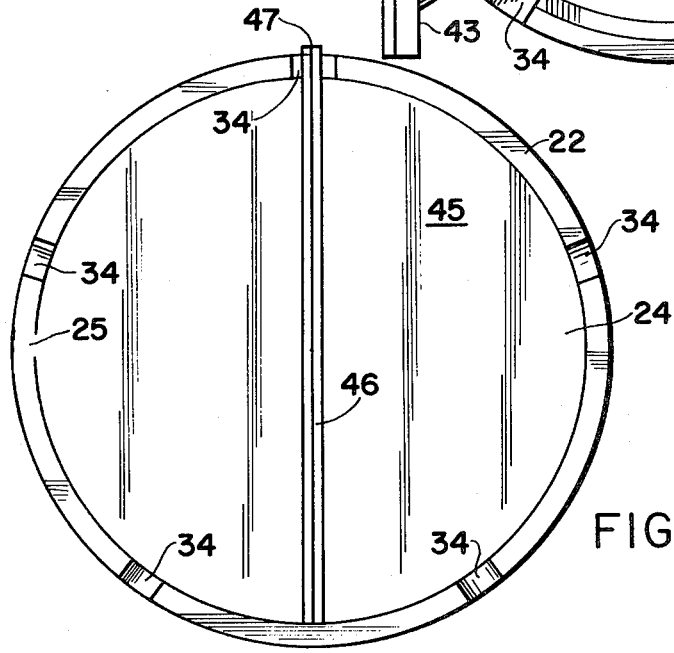

OSTOMY BAG WITH AN ADJUSTABLE VENT

FIELD OF THE INVENTION

The present invention relates to a vent for use with an ostomy bag, and, more particulary, to such a vent which is provided with a deodorizing filter. As used herein, the term "ostomy bag" will denote a colostomy bag, an ileostomy bag or any other equivalent type of bag.

BACKGROUND OF THE INVENTION

Ostomy bags are used by a person who has been provided with a surgically formed stoma (i.e., an artificial opening in the abdominal wall which serves as a discharge outlet for waste material drained from the interior of the abdominal cavity). The ostomy bag is normally attached to the wearer's abdomen opposite the stoma to collect the waste material discharged from the stoma. In order to prevent the seepage of liquid and/or solid waste from the ostomy bag, a fluid-tight connection is usually provided between the bag and wearer. Because of this fluid-tight connection, the ostomy bag may become filled with gas discharged from the stoma.

Three problems are encountered when the ostomy bag becomes inflated as a result of becoming filled with gas discharged from the stoma. First, an inflated ostomy bag creates the possibility that the bag, which is normally rather inconspicuous, could be noticeable to others through the outer clothing of the wearer. Second, the pressure created by the gas in an inflated ostomy bag can cause acute discomfort and pain to the wearer. Third, the pressure in an inflated ostomy bag can become high enough to destroy the fluid-tight connection between the bag and the wearer's abdomen, thereby releasing a foul odor and perhaps even spilling the waste material collected in the bag.

Ostomy bags have been developed which are provided with vents designed to control the inflation of the bags. Some of these vents are equipped with filters for deodorizing the air passing through the vents. Such deodorizing vents are disclosed, for example, in U.S. Pat. Nos. 4,268,286, 4,232,672, 4,211,224 and 3,759,260.

One disadvantage of the prior deodorizing vents is that the flow rate through the vents cannot be varied. The inability to vary the flow rate of the prior deodorizing vents limits their effectiveness. For instance, if the flow rate is too high, the gas may pass too quickly through the filter to be effectively deodorized.

SUMMARY OF THE INVENTION

The present invention overcomes the problems and disadvantages discussed above by providing a new and improved ostomy bag vent which is adaped to vary (i.e., make a partial change in) the rate of gas flow through the vent and, consequently, through a deodorizing filter housed in the vent. Because the flow rate through the filter can be varied, the effectiveness of the filter is enhanced. For instance, if the gas discharged from the vent has not been effectively deodorized due to an insufficient contact time with the filter, the flow rate of the gas can be decreased to thereby increase the contact time of the gas with the filter. Alternatively, the vent can be completely closed to prevent gas from flowing therethrough. The new and improved vent also permits the degree of inflation of the bag to be precisely controlled.

In one embodiment, the vent includes a housing having an interior chamber which houses the filter. The interior chamber is defined by a base and a lid, which is hinged to the base so that the filter may be removed from the interior chamber and replaced. The housing is adapted for attachment to an ostomy bag such that its interior chamber communicates with the interior of the bag. The interior chamber of the housing also communicates with the atmosphere, whereby gas in the interior of the bag can flow to the atmosphere from the interior chamber of the filter. Because the filter is housed in the interior chamber of the housing, the gas flowing through the vent will be forced to flow past and/or through the filter and thereby become deodorized.

In order to further enhance the filtering or deodorizing process, the filter can have a corrugated shape so that the gas flowing through the vent will be forced to pass through and over the filter many times before being discharged to the atmosphere. If the filter is made from a flat flexible element, such as a piece of porous cloth saturated with perfume or a sheet of foam embedded with particles of activated carbon, the lid and base of the housing may be provided with projections which cooperate to impart a corrugated shape to the normally flat filter element.

The cross-sectional area of a portion of the flow path through the vent can be varied to vary the flow rate of the gas flowing through the vent. Such variation of the cross-sectional area of the flow path can be accomplished manually by the wearer of the ostomy bag. By making the cross-sectional area of the flow path infinitely variable, fine variations of the flow rate can be achieved.

BRIEF DESCRIPTION OF THE DRAWINGS

For a more complete understanding of the present invention, reference may be had to the following description of an exemplary embodiment considered in conjunction with the accompanying drawings, in which:

FIG. 1 is an exploded perspective view of a vent constructed in accordance with the present invention and equipped for attachment to an ostomy bag;

FIG. 2 is a cross-sectional view of the vent shown in FIG. 1, the cross-section being taken through a wall of the ostomy bag to illustrate how the vent is attached to the bag;

FIG. 3 is a top view of a filter housing for the vent of FIGS. 1 and 2, the housing being shown in a closed position;

FIG. 4 is a top view of the filter housing of FIG. 3, the housing being shown in an open position;

FIG. 5 is a partial side elevational view of the filter housing of FIG. 3;

DESCRIPTION OF THE EXEMPLARY EMBODIMENT

Figure 6:
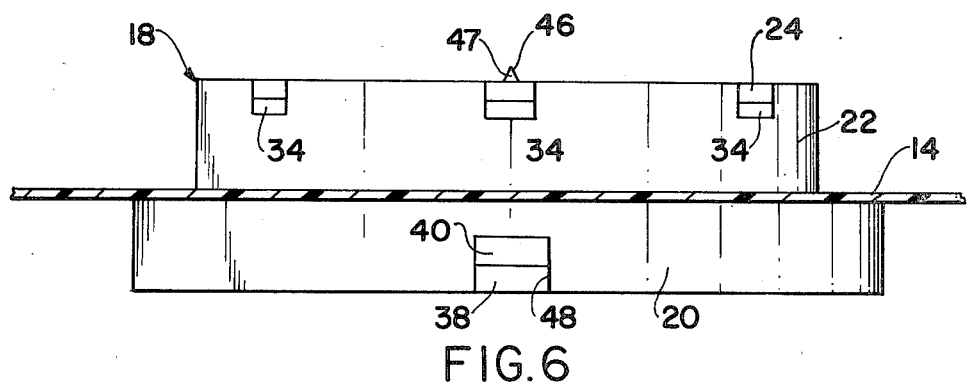
FIG. 6 is a side elevational view of the vent of FIGS. 1 and 2 in a fully open position.
Figure 7:
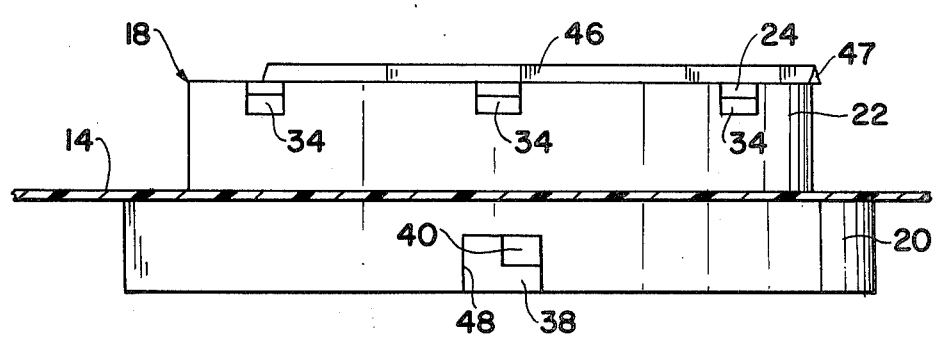
FIG. 7 is a side elevational view of the vent of FIGS. 1 and 2 in a partially open position.
Figure 8:
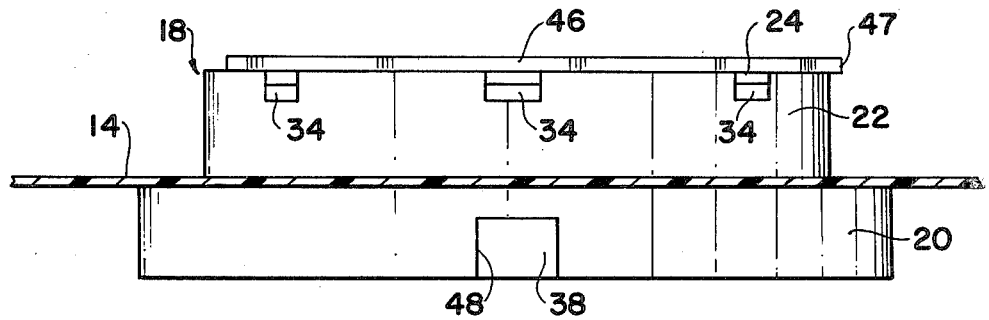
FIG. 8 is a side elevational view of the vent of FIGS. 1 and 2 in a fully closed position.

Referring to FIGS. 1-8, there is shown a conventional ostomy bag 10 which has been equipped with a unique vent 12 for venting gas, such as air, from the interior of the bag 10 to the atmosphere. More particularly, the vent 12 is applied to a front panel 14 of the bag 10. A rear panel 16 of the bag 10 is provided with an opening (not shown) adapted to surround a stoma formed in an abdominal wall of a wearer, such as colostomy patient. The front and rear panels 14, 16, respectively, are typically formed from a translucent sheet of plastic material, such as polyvinyldichloride or a laminate consisting of a layer of polyvinyldichloride sandwiched between two layers of ethylene vinyl acetate.

The vent 12 includes a housing 18 and a coupling 20 adapted to releaseably couple the housing 18 to the bag 10. The housing 18, which is preferably made of plastic, includes a base 22 and a lid 24, which is formed monolithically with the base 22 and hingedly attached thereto by, for instance, a "live" hinge 25 (see FIG. 3) so that the lid 24 can be pivoted between a closed position (see FIGS. 2, 3 and 5) and an open position (see FIGS. 1 and 4). In its closed position, the lid 24 cooperates with the base 22 to define an interior chamber 26 (see FIG. 2) in which a deodorizing filter 28 is housed. When the lid 24 is open, the deodorizing filer 28, which can be manufactured from a piece of porous cloth saturated with perfume or a sheet of foam embedded with particles of activated carbon, may be removed from the interior chamber 26 of the housing 18 and replaced. A snap fit between the base 22 and the lid 24 releaseably maintains the lid 24 in its closed postion.

The base 22 has an outer circumferential wall 30 which is provided with an annular ledge 32 and a plurality of slots 34. The ledge 32 forms a seat for the lid 24 when the lid 24 is in its closed position. Each of the slots 34 has a depth (d) which is greater than the thickness (t) of the lid 24 so that the slots 34 communicate with the interior chamber 26 of the housing 18 (see FIGS. 2 and 5). The base 22 is also provided with an annular ring 36, which projects into the interior chamber 26 of the housing 18. A plug 38 extends outwardly from the base 22. The plug 38 is provided with a slot 40, which extends diametrically across the plug 38 and communicates with the interior chamber 26 of the housing 18, and a cutting edge 42 adapted to pierce or puncture the front panel 14 of the bag 10 in a manner to be described hereinafter.

An inner side 43 of the lid 24 is provided with a pair of concentric rings 44 (see FIG. 2). When the lid 24 is in its closed position, the rings 44 project into the interior chamber 26 of the housing 18 so that the ring 36 on the base 22 is positioned between the rings 44. The ring 36 cooperates with the rings 44 to impart a corrugated shape to the normally flat filter 28 (see FIG. 2), whereby the gas flowing through the housing 18 will be forced to pass through and over the filter 28 many times before being discharged to the atmosphere. The ring 36 also cooperates with the rings 44 to hold the filter 28 in place in the interior chamber 26 of the housing 18. An outer side 45 of the lid 24 is provided with a ridge 46 which extends diametrically across the lid 24. The ridge 46 is arranged parallel to the slot 40 so that the ridge 46 can indicate the position of the slot 40 in a manner to be described hereinafter. One end 47 of the ridge 46 extends radially outwardly beyond the lid 24 and overhangs the base 22 a distance sufficient to permit the wearer to grip the end 47 of the ridge 46 and pivot the lid 24 from its closed position to its open position.

The coupling 20 is formed from a rectangular block of plastic which is fixedly attached to the inside of the front panel 14 of the ostomy bag 10 by, for instance, a suitable adhesive. The coupling 20 has a channel 48, which extends across the width of the coupling 20. A hole 50 is also provided in the coupling 20. The hole 50, which extends from the channel 48 to the front panel 14 of the ostomy bag 10, is sized and shaped so as to slideably and rotatably receive the plug 38 of the housing 18. The channel 48 communicates with the interior of the bag 10, as well as with the hole 50. By providing a bead of the adhesive around the hole 50, the portion of the ostomy bag 10 overlying the hole 50 can be made taut so as to facilitate puncturing of the front panel 14 of the bag 10 in a manner to be described hereinafter.

In initial use of the vent 12, the filter 28 is inserted into the housing 18. The housing 18 is then attached to the ostomy bag 10 by sliding the plug 38 into the hole 50 formed in the coupling 20. As the plug 38 is inserted into the hole 50, the cutting edge 42 on the plug 38 pierces or punctures the portion of the front panel 14 which overlies the hole 50.

After its attachment to the ostomy bag 10, the housing 18 can be rotated so that the slot 40 in the plug 38 communicates with the channel 48 formed in the coupling 20. When the slot 40 communicates with the channel 48, a fluid flow path (see the arrows in FIG. 2) is formed which permits air or gas to flow from the interior of the bag 10 to the atmosphere. More particularly, the flow path includes the channel 48, the slot 40 in the plug 38 of the housing 18, the interior chamber 26 of the housing 18 and the slots 34 formed in the outer wall 30 of the base 22 of the housing 18. As the air or gas flows along this flow path, it is forced to repeatedly pass over and through the filter 28 housed in the interior chamber 26 of the housing 18, whereby the air or gas is deodorized prior to its discharge to the atmosphere.

By rotating the housing 18, the wearer of the ostomy bag 10 can vary the degree of communication between the slot 40 and the channel 48 to thereby cause a variation in the cross-sectional area of this portion of the flow path and hence a corresponding variation in the flow rate through the vent 12. For instance, if maximum flow rate is desired, the housing 18 would be rotated to a position in which the slot 40 of the plug 38 is in maximum communication with the channel 48 formed in the coupling 20 (see FIG. 6). In order to decrease the flow rate through the vent 12, the housing 18 can be rotated to a position in which there is only partial communication between the slot 40 and the channel 48 (see FIG. 7). If it is desired to completely terminate the flow of gas through the vent 12, the housing 18 can be further rotated to a position in which the slot 40 does not communicate at all with the channel 48 (see FIG. 8).

Because of its parallel arrangement with the hole 40, the ridge 46 functions to indicate the various rotational positions of the hole 40 relative to the channel 48 and thereby gives the wearer an indication of the flow rate through the vent 12 at any given time. For instance, when the ridge 46 is vertical, there is maximum flow through the vent 12. A zero flow condition exists when the ridge 46 is horizontal. When the ridge is in any position besides horizontal or vertical, a partial flow condition exists through the vent 12. The ridge 46 is high enough so that it can be felt by the wearer through his or her clothing. Thus, the wearer's clothing does not have to be removed when adjusting the flow rate of the vent 12.

If it is desired to change the filter 28, the housing 18 is detached from the bag 10 by simply sliding the plug 38 out of the hole 50 formed in the coupling 20. The lid 24 can then be opened by, for instance, gripping the end 47 of the ridge 46 and pivoting the lid 24 away from the base 22. Once the lid 24 has been pivoted to its open position, the filter 28 can be removed and replaced with another filter. After the filter 28 has been replaced, the lid 24 is closed and then housing 18 is reattached to the bag 10 in the manner described previously.

It will be understood that the embodiment described herein is merely exemplary and that a person skilled in the art may make many variations and modifications without departing from the spirit and scope of the invention. All such modifications and variations are intended to be included within the scope of the invention as defined in the appended claims.

I claim:

1. In combination, an ostomy bag, having an interior portion, and a vent therefor, said vent comprising a housing; an interior chamber within said housing; a plug extending outwardly from said housing; filtering means in said interior chamber of said housing for filtering gas flowing through said housing; permitting means for permitting gas in said ostomy bag to flow through said housing to the atmosphere, said permitting means including said interior chamber of said housing, at least one opening provided in an outer edge of said housing and communicating with said interior chamber of said housing and a passageway provided in said plug and communicating with said interior chamber of said housing; coupling means fixed to said ostomy bag for releasably coupling said housing to said ostomy bag, said coupling means including a channel which is in constant communication with said interior portion of said ostomy bag and receiving means for releasably receiving said plug of said housing such that in a first position said passageway in said plug communicates with said channel in said coupling means, whereby gas in said interior of said ostomy bag may flow through said housing to the atmosphere, and in a second position said passageway in said plug does not communicate with said channel in said coupling means, whereby gas in said interior of said ostomy bag may not flow through said housing to the atmosphere; and adjusting means for adjusting the rate of gas flow through said housing.

2. A vent according to claim 1, wherein said plug is rotatably received in said receiving means of said coupling means.

3. A vent according to claim 2, wherein said adjusting means adjusts the rate of gas flow through said housing in response to the rotational movement of said housing relative to said coupling means.

4. A vent according to claim 3, wherein the degree of communication between said passageway in said plug and said channel in said coupling means is infinitely variable in response to the rotational movement of said housing relative to said coupling means.

5. A vent according to claim 1, wherein said housing includes a base and a lid hingedly attached to said base such that said lid is pivotable between a first position in which said lid cooperates with said base to form said interior chamber of said housing and a second position in which said lid is pivoted away from said base to permit said filtering means to be removed from said interior chamber and replaced.

6. A vent according to claim 1, wherein said filtering means has a corrugated shape.

7. A vent according to claim 6, wherein said filtering means is a flexible filter element.

8. A vent according to claim 7, wherein said lid includes at least one projection extending towards said base and said base includes at least one projection extending towards said lid, said projections cooperating with each other to impart a corrugated shape to said flexible filter element.

9. A vent according to claim 8, wherein said filter element is a piece of porous cloth.

10. A vent according to claim 9, wherein said porous cloth is perfumated.

11. A vent according to claim 8, wherein said filter element is a sheet of foam embedded with particles of activated carbon.

12. A vent according to claim 1, wherein said coupling means is permanently attached to an interior surface of the ostomy bag, such that a portion of the bag overlies said receiving means of said coupling means.

13. A vent according to claim 12, wherein said plug of said housing includes puncturing means for puncturing the portion of the ostomy bag overlying said receiving means of said coupling means during the insertion of said plug into said receiving means.

14. A vent according to claim 13, wherein said puncturing means is a cutting edge provided on said plug of said housing.

15. A vent according to claim 1, further comprising indicating means for indicating the rate of gas flow through said housing.

* * * * *